United States Patent
Abourizk et al.

(10) Patent No.: US 7,226,164 B2
(45) Date of Patent: Jun. 5, 2007

(54) METHOD AND APPARATUS FOR TESTING SLEEPINESS

(75) Inventors: Mark A. Abourizk, North Ryde (AU);
Paul A. Green, Lindfield (AU);
Clinton T. Stewart, Dundas (AU)

(73) Assignee: ResMed Limited, North Ryde (AU)

( * ) Notice: Subject to any disclaimer, the term of this patent is extended or adjusted under 35 U.S.C. 154(b) by 620 days.

(21) Appl. No.: 10/442,152

(22) Filed: May 21, 2003

(65) Prior Publication Data

US 2003/0218719 A1    Nov. 27, 2003

(30) Foreign Application Priority Data

May 24, 2002  (AU) .................................. PS2543

(51) Int. Cl.
*A61B 3/14* (2006.01)
(52) U.S. Cl. ..................................... 351/206
(58) Field of Classification Search ................ 351/205, 351/209, 245; 340/575, 945; 345/10; 600/558; 382/115, 181
See application file for complete search history.

(56) References Cited

U.S. PATENT DOCUMENTS

| | | |
|---|---|---|
| 4,641,349 A | 2/1987 | Flom et al. |
| 5,291,560 A | 3/1994 | Daugman |
| 5,570,698 A | 11/1996 | Liang et al. |
| 5,686,765 A | 11/1997 | Washington |

(Continued)

FOREIGN PATENT DOCUMENTS

| | | | |
|---|---|---|---|
| DE | 100 64 469 A1 | 6/2002 | |
| JP | 342337 A | * 2/1991 | .................. 180/273 |
| WO | 97/15033 A2 | 4/1997 | |

OTHER PUBLICATIONS

International Search Report mailed Jun. 26, 2003 in corresponding PCT Application No. PCT/AU03/00618.

(Continued)

*Primary Examiner*—George Manuel
(74) *Attorney, Agent, or Firm*—Nixon & Vanderhye P.C.

(57) ABSTRACT

A method and apparatus are provided for authenticating a measure of sleepiness in a person in which a measure of the person's sleepiness and an authentication step are performed substantially simultaneously on substantially the same physical attribute of the person. In one form, an eye of a person is scanned under infrared light and a unique identifying code is calculated from the iris as an authentication step. In one form, a measure of the person's sleepiness is determined from changes in the pupil size with time.

22 Claims, 4 Drawing Sheets

U.S. PATENT DOCUMENTS

| | | | |
|---|---|---|---|
| 5,729,619 A | | 3/1998 | Puma |
| 5,784,145 A | * | 7/1998 | Ghodse et al. .............. 351/205 |
| 6,097,295 A | * | 8/2000 | Griesinger et al. ......... 340/576 |
| 6,232,874 B1 | | 5/2001 | Murphy |
| 6,247,813 B1 | | 6/2001 | Kim et al. |
| 6,270,011 B1 | | 8/2001 | Gottfried |
| 6,323,761 B1 | | 11/2001 | Son |
| 6,442,465 B2 | * | 8/2002 | Breed et al. .................. 701/45 |
| 6,483,485 B1 | * | 11/2002 | Huang et al. ................. 345/10 |
| 6,882,288 B2 | * | 4/2005 | Weigl ......................... 340/945 |
| 6,927,694 B1 | * | 8/2005 | Smith et al. ................ 340/576 |
| 2002/0095076 A1 | * | 7/2002 | Krausman et al. .......... 600/323 |

OTHER PUBLICATIONS

Daugman, "How Iris Recognition Works", www.CL.cam.ac.uk/users/jgd1000 (downloaded May 2002).

Lowenstein et al, "Pupillary Movements During Acute and Chronic Fatique", Investigative Opthamology, vol. 2, No. 2, Apr. 1963, 2:138-157.

Priest et al, "Microsleep During A Simpified Maintenance of Wakefulness Test, A Validation Study of the OSLER Test", Am. J. Respir. Crit. Care Med 2001, 163: 1619-1625.

Wilhelm et al, "Pupillographic Assessment of Sleepiness in Sleep-Deprived Healthy Subjects", SLEEP, vol. 21, No. 3, 1998, 21:258-265.

* cited by examiner

METHOD AND APPARATUS FOR TESTING SLEEPINESS

FIELD OF INVENTION

The invention relates to a method and apparatus which allows an objective measure of sleepiness to be authenticated.

BACKGROUND OF INVENTION

Excessive sleepiness may result from several causes one of which is Sleep Disordered Breathing (SDB). Excessive sleepiness may be particularly dangerous for people who have to operate equipment such as cars, trucks, buses or other machinery. There have been number of fatal accidents recently where truck drivers have fallen asleep at the wheel. It has been subsequently established that the drivers suffered from sleep apnea. Fatigue in general has been identified as a cause of vehicle accidents. It has been suggested that sleepiness or wakefulness tests would be a requirement for drivers before they are allowed to start a long drive or periodically in order to renew their licence, particularly those who have been diagnosed with sleep apnea.

There are a number of tests to measure sleepiness such as the Epworth Sleepiness scale tests, Vigilance tests and Pupillometry.

The Epworth Sleepiness Scale test is based on a series of questions which are asked of the patient. In some forms, the questions may be posed by an administrator who is physically present while the patient answers. In other forms, the questions may be remotely posed, for example, for self assessment via regular mail, the internet or via an embedded device such as the Health Buddy manufactured by Health Hero.

Vigilance tests measure a patient's reaction time and cognitive alertness, which are generally understood to be indicative of a patient's sleep propensity. This type of test is typically administered using a personal computer (PC) and requires that the patient provide responses to displayed indicia via the input devices associated with the PC. The patient's reaction time in providing the response and/or the accuracy of the response to the displayed indicia are measured and stored to determine the patient's level of alertness. For example, the patient is shown a recognizable object on the PC display, and the patient's reaction time in identifying the object and the accuracy of the identification are measured. One form of vigilance test is to have the person perform a repetitive task, such as clicking a button with a finger upon a signal and to monitor the reaction time or accuracy with which the person clicks the button when signaled to do so.

One form of wakefulness test using a finger-based test is described in "Microsleep during a Simplified Maintenance of Wakefulness Test: A Validation Study of the OSLER Test" by Priest et al. in Am. J. Respir Crit Care Med Volume 163, pp16190-1625, 2001.

One form of fingerprint identification unit is the "Sony Fingerprint Identification Unit" FIU-710.

Pupillometry is based on the observation that the pupils of sleepy individuals display measurable characteristics which are significantly different to the pupils of people who are not sleepy. During pupillometry recording in the dark, the pupils of behaviorally sleepy individuals oscillate widely in size. This phenomenon is named pupillary "fatigue waves", and is not observed in people who are not sleepy. Low-frequency components are dominant in persons with excessive daytime sleepiness. The amplitude of slow oscillations (typically less than 0.5 Hz) can reach several millimeters. It has also been observed that the pupils of sleepy people became increasingly miotic (decreased in size) with ensuing sleepiness. In contrast the pupils of people who are behaviorally alert maintain a stable size. The phenomenon has been observed by Lowenstein and colleagues and reported in an article entitled "Pupillary movements during acute and chronic fatigue" published in Investigative Opthalmology, 2, 138-157 (1963).

In the article "Pupillographic Assessment of Sleepiness in Sleep-deprived Healthy Subjects" in the SLEEP journal, volume 32, no. 3, 1998 by Wilhelm et al., a method of providing sleepiness measures is described. The contents of this article are hereby incorporated by reference.

In this specification, the term "sleepiness test" is intended to include somnolence and wakefulness tests.

A potential difficulty with the use of these tests in certain applications is that of authenticating the person who is being tested. This may be critical in applications where the person may be required to operate potentially dangerous equipment, such as truck driving, where there may be an incentive for the person to work in spite of being tired. For example, if the Epworth Sleepiness Scale test were to be administered remotely, the person may ask another, presumably non-tired, non-sleepy or more wakeful person to take the test instead and there may be no way to verify who has taken the test. An automatic system for sleepiness testing may be capable of correctly identifying whether or not a person is sufficiently alert to drive, or to undertake a particular task such as operating machinery, however, the system may be defeated if a substitute person takes the sleepiness test.

Similarly sleepiness testing may be administered on a periodic basis to determine whether a user has been compliant with a medical treatment for their condition. A determination of compliance can be useful as part of management of their condition. A user's compliance with medical treatment may also be a precondition for the grant or maintenance of a permit such as a driver's licence. Therefore it would be desirable for a sleepiness test to be conducted on a periodic basis in a location convenient to the user and preferably without the need of attendance by a skilled operator. Ideally the sleepiness test will be capable of self administration by the user.

It is one aspect of the invention to overcome problems with prior art sleepiness tests.

SUMMARY OF THE INVENTION

One aspect of the present invention is to provide a method and apparatus whereby a sleepiness test is conducted on a person substantially simultaneously with an authentication technique on the person using the same or a similar physical feature of the person.

Another aspect of the invention is to provide a method and apparatus whereby a scan is performed on an eye of a person to calculate eye scan data and both an authentication step and a sleepiness measure are calculated on the eye scan data.

In another aspect of the invention, sleepiness is measured using pupillometry and authentication is performed using an iris scan of the same eye. In yet another aspect of the invention, vigilance is measured using a repetitive finger-based cognitive test, while finger-print scanning is performed on the same finger.

Another aspect of the invention is that the sleepiness and authentication measurements are performed on physically similar features to reduce the likelihood that the sleepiness test could be administered to one person while the authentication is performed on another person.

Another aspect of the invention provides that the sleepiness and authentication measurements are performed either simultaneously, or in rapid succession, for example, with micro- or milli-seconds between measurements.

DETAILED DESCRIPTION OF THE ILLUSTRATED EMBODIMENTS

Figure 1:
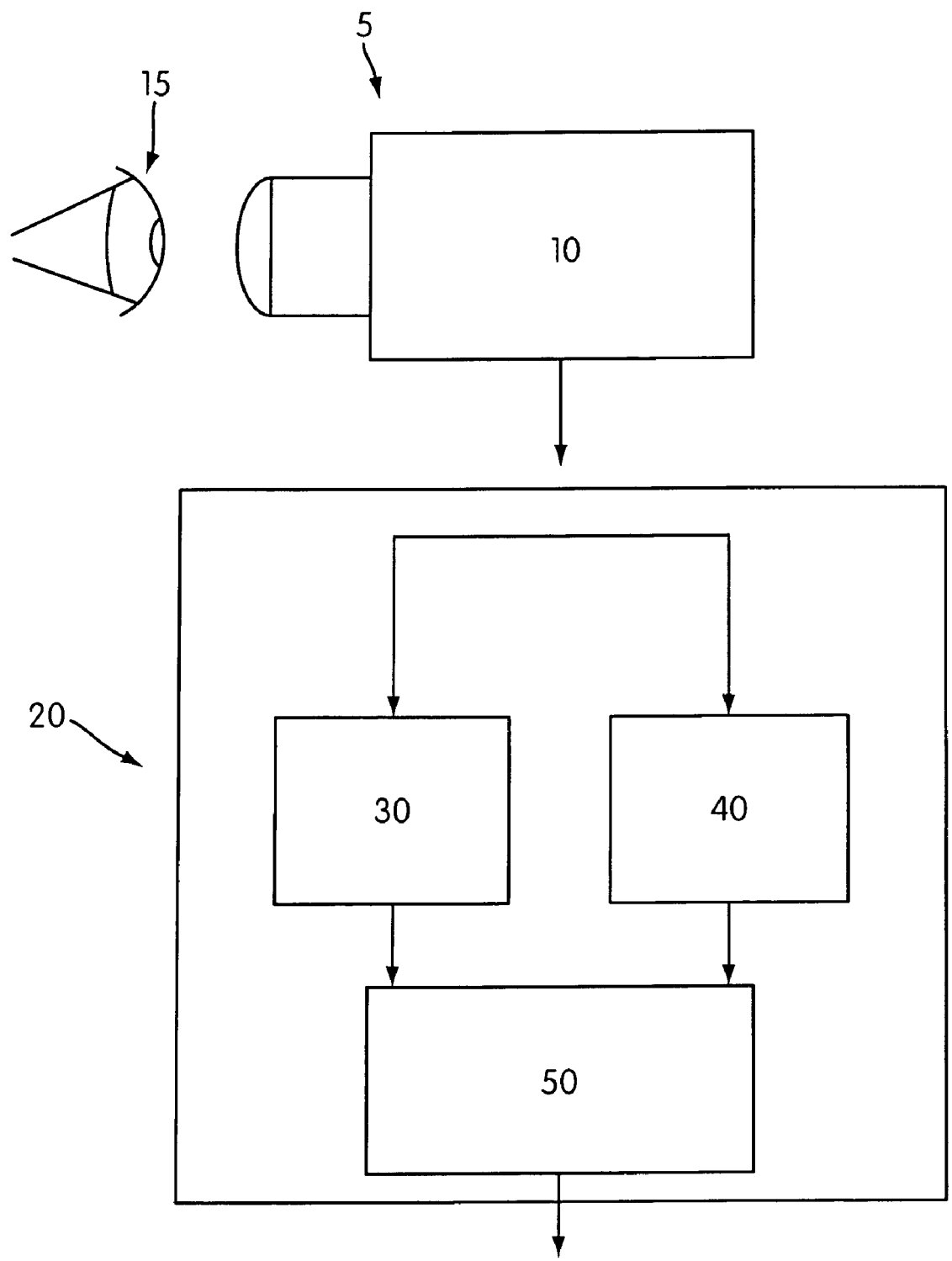
FIG. 1 is a schematic view of an embodiment of an apparatus structured to conduct a sleepiness test and an authentication technique on a person.

FIG. 1 illustrates one embodiment of an apparatus 5 structured to conduct a sleepiness test and an authentication technique on a person. The apparatus 5 comprises a digital camera 10 connected to a computer 20 that is structured to substantially simultaneously conduct pupillometry for the sleepiness test and iris scan identification for the authentication technique. In one form, "substantially simultaneously" means within a time period of small enough magnitude which would make it physically impossible/difficult to substitute the tested physical feature between the authentication step and the sleepiness testing step.

In the illustrated embodiment, the computer 20 includes an authentication software module 30, a sleepiness software module 40, and a certification software module 50. The digital camera 10 may be a monochrome camera with a CCD with a resolution of 480×640 pixels to provide the scan. A low light level is used. The camera 10 scans at a frequency of approximately 30 f.p.s., hence images of the eye are taken within 1/30th of a second of one another. In one embodiment, the person to be tested is provided with the visual feedback on a separate monitor of the camera image and instructed to position themselves so as to present an eye 15 to the camera 10. The image is automatically checked to ensure that it is in focus. If it is in focus, then the position of the iris within the image data is automatically determined. The same frame of iris data is then sent to both the authentication software module 30 and the sleepiness software module 40.

Generally, light wavelengths in the visible spectrum (400 nm to 750 nm) and portions of the near-infrared spectrum up to 1100 nm are able to be detected by a CCD based image sensor. In one embodiment, the camera for taking images of the eye may be the ToUCam Pro PCVC740K manufactured by Philips Electronics. This camera uses a CCD imaging sensor. The camera is connected to a personal computer via a USB cable. The images from the camera are stored as bitmaps.

Figure 2:
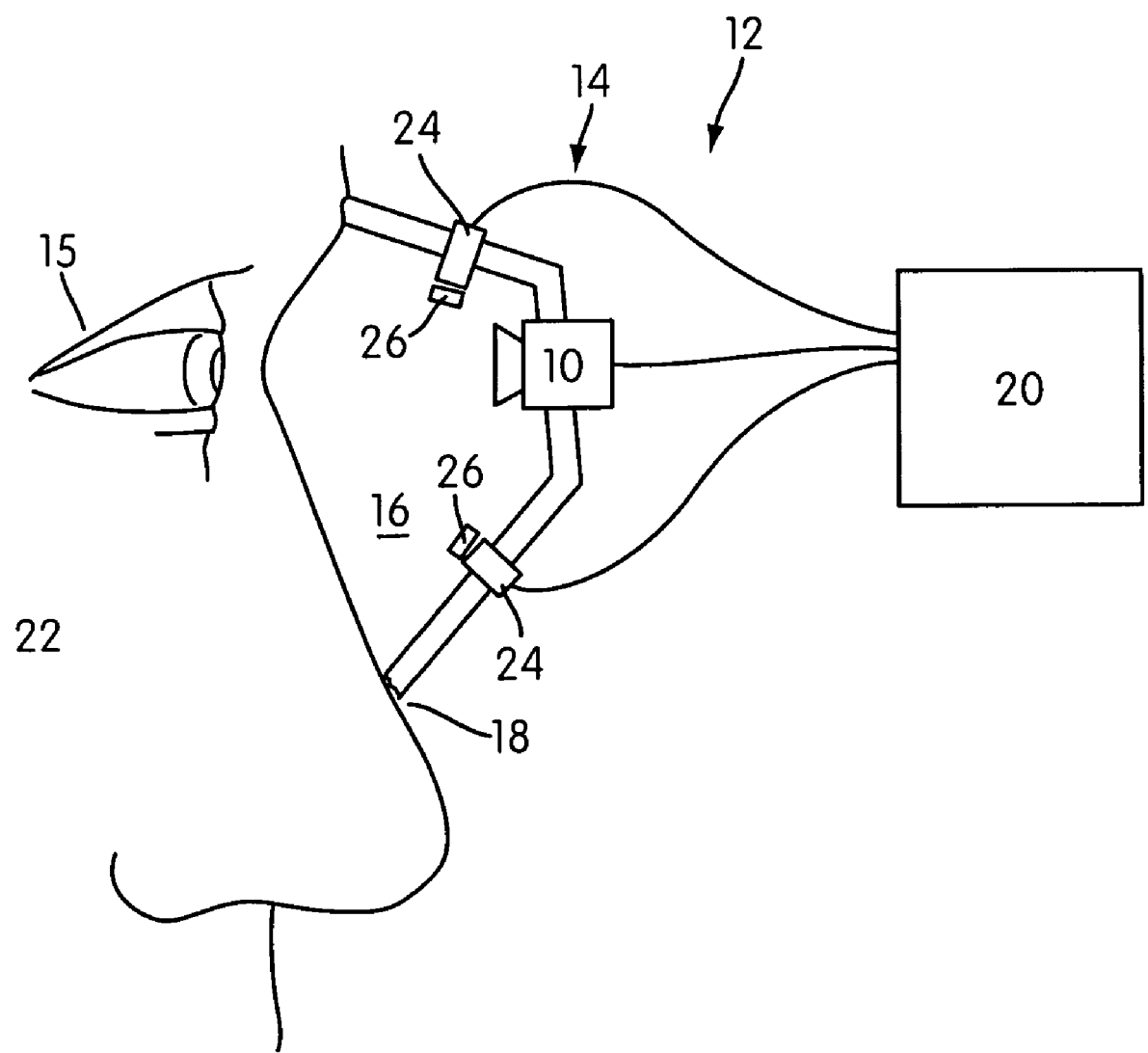
FIG. 2 is a schematic view of the apparatus shown in FIG. 1 positioned over a person's eye.

In the embodiment shown in FIG. 2, a camera 10 is mounted on a frame 12 which supports the camera and makes it wearable. A hood 14 is provided which projects from the camera and which serves to isolate the eye 15 from incident light. In this way the amount of light which falls on the eye can be controlled. If there is too much light falling on the eye, it may be difficult to monitor sleepiness. However, if there is too little light falling on the eye, the pupil may dilate to such a degree that it may be difficult to scan the iris of the eye for authentication.

The hood defines a chamber 16. The hood has a soft, comfortable edge 18 which in use is positioned against the face of the person 22. The soft edge 18 of the hood 14 may be constructed from a material such as silicone. The chamber includes lights 24 positioned to illuminate the eye 15 at a predetermined light level for the eye to be scanned, but not so bright as to cause the iris to be too small for authentication. The lights are arranged to minimize light reflections in the scanned image. The lights provide a diffuse light source so as to provide a soft, even illumination of the eye. In one embodiment, a diffuser 26 is positioned over the light.

In one embodiment, the lights may be infrared light emitting diodes, for example HE8807FL manufactured by Hitachi Ltd.

In one embodiment of the invention, scans are taken at different lighting levels. For example, a low level of illumination is used for a first series of scans and then a second, higher level of illumination is used for a second series of scans. In another embodiment, the high level of illumination is used before the low level of illumination.

When the hood 14 first covers the eye, it may take some time, for example 3 minutes, for the pupil to adapt to the low level of lighting which is provided by the lights. During this adaptation time, a series of scans of the eye are made to monitor the adaptation. In this way the apparatus can determine when the eye is ready to perform the authenticated sleepiness measurements.

Figure 3:
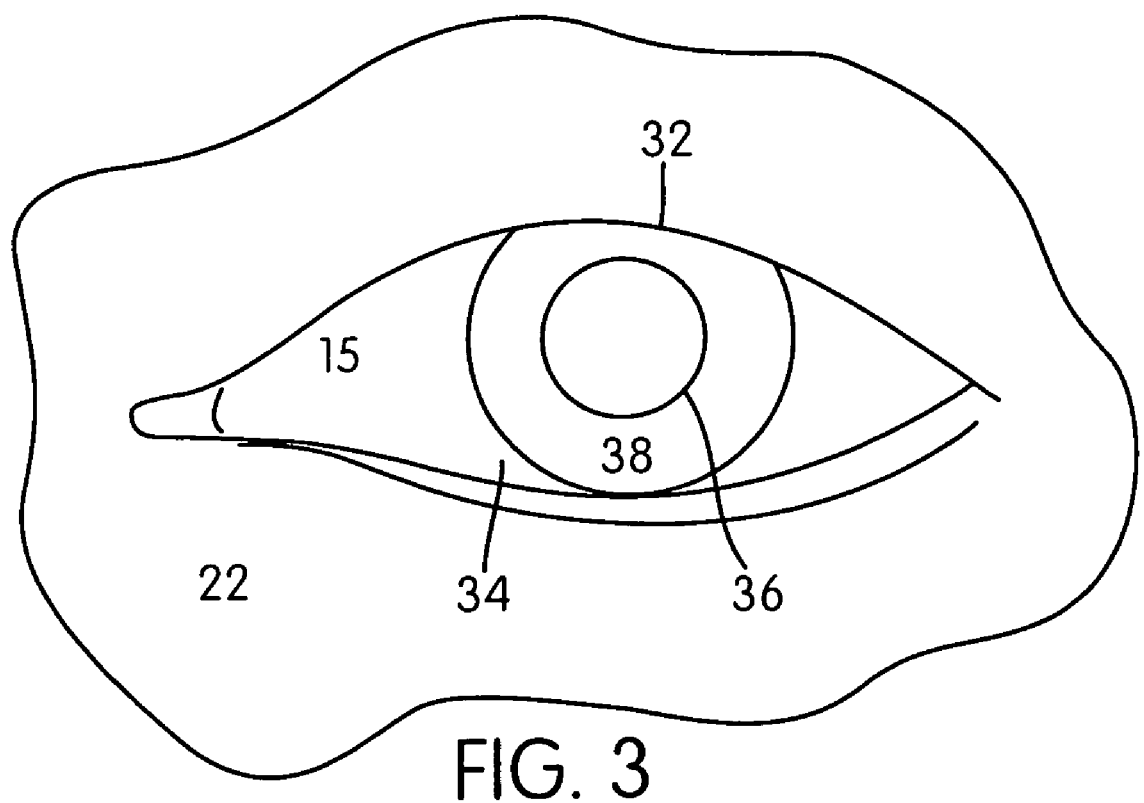
FIG. 3 shows a scanned eye of a person including an iris (reproduced from "How Iris Recognition Works", Daugman J, www.cl.cam.ac.uk/users/jgd1000/)
Figure 4A:
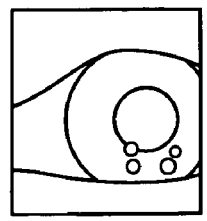
FIGS. 4(a)-4(d) show images of an eye with different pupil diameters (reproduced from "Measuring Sleepiness with Pupillometry", www.uic.edu/depts/cnr/CNRPupillometer.htm).
Figure 4B:
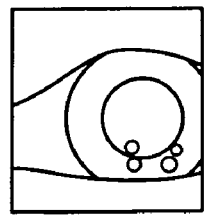
Figure 4C:
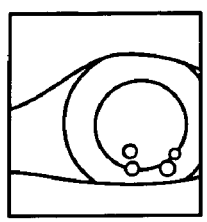
Figure 4D:
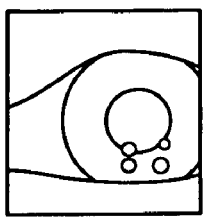

FIG. 3 shows an eye 15. The iris 38 has been automatically detected and recognized within the image. In the authentication software module 30, each isolated iris pattern is then demodulated to extract its phase information using quadrature 2D Gabor wavelets, for example, as described in U.S. Pat. No. 5,291,560 (Daugman), the contents of which are hereby incorporated by reference. This technique provides a distinctive 256-byte code which may be used to authenticate the iris of the person.

As shown in FIG. 3, the inner 36 and outer 34 edges of the iris 38 are automatically detected and recognized within the image of the eye. In the sleepiness module 40, the size of the pupil is measured and recorded with respect to time. An index of sleepiness is derived from the size of the pupil and oscillations in pupil diameter. In a sleepy person, there are relatively large changes in pupil diameter. In one embodiment, the pupil diameter versus time data is transformed into a frequency versus power form via a Fast Fourier transform. Sleepy individuals exhibit peak powers at characteristic frequencies such as 1 Hz. A sleepiness index may be derived from the total power of signals in the region of 1 Hz.

FIG. 4 shows a series of four images of an eye. In the different images (a), (b), (c) & (d), the pupil has different sizes. The inner and outer edges of the iris are automatically detected and the rate of change of the size of the pupil is determined.

In one embodiment of the invention, the following algorithm may be performed:

Perform a first scan of the eye,
Identify features of the eye from the first scan,
Calculate a first code based on the features identified from the first scan, Measure the size of the pupil from the first scan;

Perform a second scan of the eye,

Identify features of the eye from the second scan,

Calculate a second code based on the features from the second scan,

Measure the size of the pupil from the second scan;

Compare the first and second codes to determine whether the eyes used in the first and second scans are the same, similar or different;

If the same eye has been confirmed to be used in both scans, calculate the rate of change of pupil size between the first and second scans.

The first and second scans may be interposed with other scans. A series of scans may be performed over a period of time, for example 10 minutes, in order to conduct accurate pupillometry measurements.

In one embodiment of the invention, the pupillometry and authentication steps may be performed in real time, that is, as soon as a scan is made of the eye, the images are sent to the software modules for calculations. In another embodiment of the invention, images of the eye may be time and date stamped and stored in a memory unit for later analysis.

In one embodiment of the invention, image analysis may be performed in the same location as the person being scanned. In another embodiment of the invention, the scanned images may be transmitted to a remote location and image analysis is conducted at the remote location.

In one embodiment of the invention, the results of the authentication process may be compared with a database. For example, iris scan or fingerprint scanning results may be compared to a database having names, addresses and other bibliographic information. In this way the identification of the person who is being scanned can be confirmed.

In another embodiment of the invention, sleepiness may be determined from blink rate, For example, as described in U.S. Pat. Nos. 5,570,698 or 6,097,295, the contents of both of which are hereby incorporated by reference.

In another embodiment of the invention, the sleepiness and authentication tests may be performed on a persons finger. Fingerprint scanning may be performed using a technique such as described in U.S. Pat. No. 6,270,011.

Once both the authentication test and sleepiness test have been performed, the results are sent to the certification software module 50. This module provides a signed certificate in physical or electronic form which certifies the result of the sleepiness test, matched to the authentication result. When provided in digital form, the data may be signed electronically using a technique such as public key cryptography as provided by the PGP programme by Philip Zimmerman. In one embodiment, the data may be emailed to a time stamping service such as that provided by the UK firm, IT Consult. In one embodiment, the camera may provide image data together with a serial number which identifies the imaging chip of the camera to the certification software modules. In one embodiment, the certificate may be sent to a database electronically via a network connection. In another embodiment, the authentication test may be cross checked with a database to add bibliographic information of the person performing the test to the certificate.

In one embodiment of the invention, an authentication step may be performed on the person at a first time, a measure of sleepiness is performed over a period of time and a test is performed to determine whether the person has moved from the test apparatus. For example, initially, the iris of the person is scanned and thereafter the sleepiness test is performed over time, no further iris scanning is performed during the sleppiness test, however, the eye being scanned is monitored to determine whether the eye moves away from the camera. If the eye moves away from the camera or there is a significant shift of the eye in the view of the camera, a new authentication step is performed on the iris of the person.

In one embodiment of the invention, the authentication and sleepiness tests may not be performed on exactly the same eye scan data, however, they may be performed on eye scan data which have been determined very close in time to one another. For example, a first scan may be conducted and an authentication step is performed on the data from the first scan. Soon after the first scan, a second scan is performed and the sleepiness test is performed on data from the second scan. This use of sequential scans may continue for the duration of the sleepiness test. The time delay between the first and second scans is short, for example less than a second, so as not to allow the sleepiness and authentication steps to be performed on different people.

In another embodiment of the invention, an additional authentication step may be used. For example, while sleepiness and authentication steps are being performed on an eye of a person, a fingerprint scan of the person may also be conducted. The results from both the iris scan and the fingerprint scan may be used to identify or characterize the person being tested.

Although the invention has been described with reference to a particular embodiment, it is to be understood that this embodiment is merely illustrative of the principles of the invention. Thus, it is to be understood that numerous modifications may be made in the illustrative embodiment of the invention and other arrangements may be devised without departing from the spirit and scope of the invention.

The invention claimed is:

1. A method of authenticating a measure of sleepiness in a person, the method comprising:
    measuring a person's sleepiness; and
    performing an authentication step substantially simultaneously with measuring a person's sleepiness, wherein the person's sleepiness and the authentication step are performed on substantially the same physical attribute of the person.

2. A method as claimed in claim 1, wherein the measuring of a person's sleepiness is determined by pupillometry and the performing an authentication step is determined by iris scanning.

3. A method as claimed in claim 1, wherein the physical attribute of the person is an eye of the person.

4. A method as claimed in claim 1, wherein the measuring of a person's sleepiness and the performing of an authentication step are performed within $\frac{1}{30}$th of a second of one another.

5. A method as claimed in claim 1, wherein a result of the measuring of a person's sleepiness and the performing of an authentication step is certified.

6. A method as claimed in claim 1, wherein the physical attribute of the person is a finger of the person.

7. A method of authenticating a measure of sleepiness in a person, the method comprising:
    illuminating an eye of the person by an infrared light;
    measuring a person's sleepiness by the eye by imaging using said light; and
    performing an authentication step by the eye to determine the person's identity based on said imaging.

8. An apparatus for authenticating sleepiness measurements, comprising:
   camera; and
   a computer having a sleepiness measuring software module and an eye authentication software module,
   wherein the camera is adapted to scan the eye of a person and provide an image to both the sleepiness measuring software module and to the eye identification software module.

9. The apparatus as claimed in claim 8, further comprising a frame adapted to mount the camera in front of an eye of a person.

10. The apparatus as claimed in claim 8, further comprising a hood defining a chamber, the hood adapted to seal the eye of a person against incident light exterior of the chamber from illuminating the eye.

11. The apparatus as claimed in claim 8, wherein the sleepiness measuring software module is programmed to measure a rate of change of a pupil diameter.

12. The apparatus as claimed in claim 8, wherein the sleepiness measuring software module is programmed to measure a blink rate of a person.

13. The apparatus as claimed in claim 8, wherein the eye authentication software module is programmed to scan an image of an iris of the eye and calculate an identifying code from the image of the iris.

14. An apparatus for authenticating sleepiness measurements, comprising:
   a camera structured to scan an eye of a person;
   a frame constructed and arranged to position the camera in front of the eye of the person in use;
   a hood structured to shield the eye from illumination by an external source of light in use; and
   at least one light structured to illuminate the eye of the person at at least one predetermined level of illumination in use,
   wherein the camera is structured to provide an image of an iris of the eye of the person in a form suitable for calculating an identifying code of the iris,
   wherein the hood is structured to be wearable by the person in use, and
   wherein the hood includes at least one portion that is structured to engage the person in use.

15. The apparatus as claimed in claim 14, further comprising a diffuser positioned over the at least one light.

16. The apparatus as claimed in claim 14, wherein the at least one light is an infrared light.

17. A method of authenticating a measure of sleepiness on an eye of a person, the method comprising:
   performing a first scan of the eye;
   identifying first features of the eye from the first scan;
   calculating a first code based on the first features identified from the first scan;
   measuring a first pupil size of the eye from the first scan;
   performing a second scan of the eye;
   identifying second features of the eye from the second scan;
   calculating a second code based on the second features from the second scan;
   measuring a second pupil size of the eye from the second scan; and
   comparing the first and second codes to determine whether the eye used in the first and second scans are the same.

18. The method as claimed in claim 17, further comprising:
   calculating a rate of change of pupil size between the first and second scans if the same eye has been confirmed to be used in both scans.

19. The method as claimed in claim 17, wherein identifying first and second features includes identifying an iris of the person.

20. The method as claimed in claim 17, further comprising determining a power of low frequency oscillations in pupil size.

21. A method of authenticating a measure of sleepiness in a person, the method comprising:
   performing pupillometry on an eye of the person to determine an index of sleepiness;
   performing iris scanning on the eye of the person to determine a code for authentication; and
   certifying that the index of sleepiness is matched with the code for authentication.

22. The method as claimed in claim 21, wherein the performing pupillometry and the performing iris scanning are performed substantially simultaneously.

* * * * *

UNITED STATES PATENT AND TRADEMARK OFFICE
CERTIFICATE OF CORRECTION

PATENT NO. : 7,226,164 B2
APPLICATION NO. : 10/442152
DATED : June 5, 2007
INVENTOR(S) : Abourizk et al.

It is certified that error appears in the above-identified patent and that said Letters Patent is hereby corrected as shown below:

Column 6, claims 1 and 4, should read:

1. A method of authenticating a measure of sleepiness in a person, the method comprising:
measuring a person's sleepiness using image analysis, and
performing an authentication step to determine the person's identity substantially simultaneously with measuring the person's sleepiness, wherein the person's sleepiness and the authentication step are performed using image analysis on substantially the same physical attribute of the person.

4. A method of authenticating a measure of sleepiness in a person, the method comprising:
measuring a person's sleepiness; and
performing an authentication step to determine the person's identity substantially simultaneously with measuring the person's sleepiness, wherein the person's sleepiness and the authentication step are performed on substantially the same physical attribute of the person, wherein the measuring of a person's sleepiness and the performing of an authentication step are performed within $1/30^{th}$ of a second of one another.

Column 7, claims 8 and 14, should read:

8. An apparatus for authenticating sleepiness measurements, comprising:
camera; and
a computer having a sleepiness measuring software module and an eye authentication software module to determine a person's identity and amount of sleepiness,
wherein the camera is adapted to scan the eye of a person and provide an image to both the sleepiness measuring software module and to the eye identification software module.

Signed and Sealed this
Twenty-second Day of March, 2011

David J. Kappos
*Director of the United States Patent and Trademark Office*

14. An apparatus for authenticating sleepiness measurements, comprising:
a camera structured to scan and image an eye of a person;
a frame constructed and arranged to position the camera in front of the eye of the person in use;
a hood structured to shield the eye from illumination by an external source of light in use; and
at least one light structured to illuminate the eye of the person at at least one predetermined level of illumination in use,
wherein the camera is structured to provide an image of an iris of the eye of the person in a form suitable for calculating an identifying code of the iris and to measure sleepiness,
wherein the hood is structured to be wearable by the person in use, and
wherein the hood includes at least one portion that is structured to engage the person in use.

Column 8, claims 17 and 21, should read:

17. A method of authenticating a measure of sleepiness on an eye of a person, the method comprising:
performing a first scan of the eye;
identifying first features of the eye from the first scan;
calculating a first code based on the first features identified from the first scan;
measuring a first pupil size of the eye from the first scan;
performing a second scan of the eye;
identifying second features of the eye from the second scan;
calculating a second code based on the second features from the second scan;
measuring a second pupil size of the eye from the second scan;
comparing the first and second codes to determine whether the eye used in the first and second scans is the same; and
comparing said first and second features or measured pupil sizes to measure sleepiness.

21. A method of authenticating a measure of sleepiness in a person, the method comprising:
performing pupillometry on an eye of the person to determine an index of sleepiness;
performing iris scanning on the eye of the person to determine a code for authentication to determine the person's identity; and
certifying that the index of sleepiness is matched with the code for authentication of the person's identity.

UNITED STATES PATENT AND TRADEMARK OFFICE
CERTIFICATE OF CORRECTION

PATENT NO. : 7,226,164 B2
APPLICATION NO. : 10/442152
DATED : June 5, 2007
INVENTOR(S) : Abourizk et al.

It is certified that error appears in the above-identified patent and that said Letters Patent is hereby corrected as shown below:

Column 6, lines 36-44, claim 1 should read:

1. A method of authenticating a measure of sleepiness in a person, the method comprising:
measuring a person's sleepiness using image analysis, and
performing an authentication step to determine the person's identity substantially simultaneously with measuring the person's sleepiness, wherein the person's sleepiness and the authentication step are performed using image analysis on substantially the same physical attribute of the person.

Column 6, lines 52-55, claim 4 should read:

4. A method of authenticating a measure of sleepiness in a person, the method comprising:
measuring a person's sleepiness; and
performing an authentication step to determine the person's identity substantially simultaneously with measuring the person's sleepiness, wherein the person's sleepiness and the authentication step are performed on substantially the same physical attribute of the person, wherein the measuring of a person's sleepiness and the performing of an authentication step are performed within $1/30^{th}$ of a second of one another.

Column 7, lines 1-9, claim 8 should read:

8. An apparatus for authenticating sleepiness measurements, comprising:
camera; and
a computer having a sleepiness measuring software module and an eye authentication software module to determine a person's identity and amount of sleepiness, This certificate supersedes the Certificate of Correction issued March 22, 2011.

Signed and Sealed this
Twenty-sixth Day of April, 2011

David J. Kappos
*Director of the United States Patent and Trademark Office* wherein the camera is adapted to scan the eye of a person and provide an image to both the sleepiness measuring software module and to the eye identification software module.

Column 7, lines 27-43, claim 14 should read:

14. An apparatus for authenticating sleepiness measurements, comprising:
a camera structured to scan and image an eye of a person;
a frame constructed and arranged to position the camera in front of the eye of the person in use;
a hood structured to shield the eye from illumination by an external source of light in use; and
at least one light structured to illuminate the eye of the person at at least one predetermined level of illumination in use,
wherein the camera is structured to provide an image of an iris of the eye of the person in a form suitable for calculating an identifying code of the iris and to measure sleepiness,
wherein the hood is structured to be wearable by the person in use, and
wherein the hood includes at least one portion that is structured to engage the person in use.

Column 8, lines 3-20, claim 17 should read:

17. A method of authenticating a measure of sleepiness on an eye of a person, the method comprising:
performing a first scan of the eye;
identifying first features of the eye from the first scan;
calculating a first code based on the first features identified from the first scan;
measuring a first pupil size of the eye from the first scan;
performing a second scan of the eye;
identifying second features of the eye from the second scan;
calculating a second code based on the second features from the second scan;
measuring a second pupil size of the eye from the second scan;
comparing the first and second codes to determine whether the eye used in the first and second scans is the same; and
comparing said first and second features or measured pupil sizes to measure sleepiness.

Column 8, lines 33-40, claim 21 should read:

21. A method of authenticating a measure of sleepiness in a person, the method comprising:
performing pupillometry on an eye of the person to determine an index of sleepiness;
performing iris scanning on the eye of the person to determine a code for authentication to determine the person's identity; and
certifying that the index of sleepiness is matched with the code for authentication of the person's identity.